United States Patent
Maehara et al.

(10) Patent No.: US 7,250,535 B2
(45) Date of Patent: Jul. 31, 2007

(54) PROCESS FOR PRODUCING TERTIARY PHOSPHINE

(75) Inventors: Shinya Maehara, Atsugi (JP); Hideyuki Iwazaki, Atsugi (JP)

(73) Assignee: Hokko Chemical Industry Co., Ltd., Tokyo (JP)

( * ) Notice: Subject to any disclaimer, the term of this patent is extended or adjusted under 35 U.S.C. 154(b) by 255 days.

(21) Appl. No.: 10/503,577

(22) PCT Filed: Feb. 3, 2003

(86) PCT No.: PCT/JP03/01055

§ 371 (c)(1), (2), (4) Date: Aug. 4, 2004

(87) PCT Pub. No.: WO03/066643

PCT Pub. Date: Aug. 14, 2003

(65) Prior Publication Data

US 2006/0020148 A1    Jan. 26, 2006

(30) Foreign Application Priority Data

Feb. 4, 2002 (JP) ............... 2002-026490
Feb. 19, 2002 (JP) ............... 2002-041204

(51) Int. Cl.
*C07F 9/02* (2006.01)
(52) U.S. Cl. .......................................... 568/9
(58) Field of Classification Search .................. 568/9
See application file for complete search history.

(56) References Cited

U.S. PATENT DOCUMENTS 6,307,087 B1    10/2001    Buchwald et al.
2002/0165411 A1*    11/2002    Hartwig et al. ............ 564/15

FOREIGN PATENT DOCUMENTS

WO    WO 99/09040 A1    2/1999
WO    WO 02/48160 A1    6/2002

OTHER PUBLICATIONS

Aranyos, Attila et al., "Novel Electron-Rich Bulky Phosphine Ligands Facilitate the Palladium-Catalyzed Preparation of Dairyl Ethers", *Journal of the American Chemical Society*, 1999, pp. 4369-4378, vol. 121 (10 pp.), USA.
Wolfe, John P. et al., "Simple, Efficient Catalyst System for the Palladium-Catalyzed Amination of Aryl Chlorides, Bromides, and Triflates", *Journal of Organic Chemistry*, 2000, pp. 1158-1174, vol. 65 (17 pp.), USA.
Kaye, Steven et al., "The Use of Catalytic Amounts of CuCI and Other Improvements in the Benzyne Route to Biphenyl-Based Phosphine Ligands", *Advanced Synthesis & Catalysis*, 2001, pp. 789-794, vol. 343, No. 8 (6 pp.), Germany.
Hoffmann, Hellmut et al., "Preparation of Tri-tert-butylphosphine", *Chemische Bertichte*, (Journal in German language) 1967, pp. 692-693 with English abstract, Germany.
Kim, Dae-Hyun et al., "Synthesis and Characterization of o-Carboranylmethylenephosphine, Crystal Structure of $(C_2B_{10}H_{11})CH_2PBu^*_2$ and $(C_2B_{10}H_{11})CH_2PMe_2$", *Bulletin of the Korean Chemical Society*, 1999, pp. 600-604, vol. 20, No. 5, Korea (5 pp.).
Crofts, P.C. et al., "Tertiary-Pentyl Phosphorus Compounds", *Journal of the Chemical Society (C)*, 1970, pp. 2529-2530, (2 pp.).
Corfield, J.R. et al., "The Alkaline Hydrolysis of Sterically Crowded Phosponium Salts", *Journal of the Chemical Society (C)*, 1971, pp. 1930-1933 (4 pp.), UK.
Bartsch, Rainer et al., "Alkyl- and Aryfluorophosphines as ligands in transition metal complexes with metals in the positive oxidation state, IV. Ligand exchange and redox reactions of iron-, cobalt-, and nickel halide complexes", *Chemische Berichte*, 1978, pp. 1420-1433, vol. 111, (14 pp. plus English abstract), Germany.
Stephens, R.D., "Transition Metal Compounds and Complexes, 17. Hydrido(Triphenylphosphine)Copper(I)", *Inorganic Synthesis*, Chapter Three: Transition Metal Compounds and Complexes, 1979, pp. 87-89 (3 pp.).

* cited by examiner

*Primary Examiner*—Joseph K. McKane
*Assistant Examiner*—Yong Chu

(57) ABSTRACT

A production process by which tertiary phosphine with an attached sterically bulky hydrocarbon group is produced in a high yield and with high purity on an industrial scale through simple and safe operations by allowing a dialkylphosphinous halide to react with a Grignard reagent in the presence of a copper compound in an amount corresponding to 0.1 to 5% by mol based on the dialkylphosphinous halide to produce tertiary phosphine represented by the following formula (3):

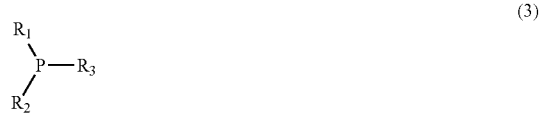

(3)

wherein $R_1$ and $R_2$ are each a tertiary hydrocarbon group of 4 to 13 carbon atoms, and $R_3$ is an alkyl group, an alkenyl group, an aryl group or the like.

21 Claims, No Drawings

PROCESS FOR PRODUCING TERTIARY PHOSPHINE

TECHNICAL FIELD

The present invention relates to a process for producing tertiary phosphine with an attached sterically bulky hydrocarbon group. More particularly, the invention relates to a process wherein tertiary phosphine with an attached sterically bulky hydrocarbon group, which is useful as a ligand of a transition metal catalyst in organic synthesis reactions, is produced in a high yield and with high purity on an industrial scale through simple and safe operations.

BACKGROUND ART

In recent years, there have been reported a large number of organic synthesis reactions using transition metal catalysts obtained by coordinating tertiary phosphine with a sterically bulky hydrocarbon group such as a tert-butyl group or an adamantyl group to transition metals such as palladium (see, for example, "Journal of the American Chemical Society" (U.S.A.), 1999, vol. 121, pp. 4369-4378, "Journal of the Organic Chemistry" (U.S.A.), 2000, vol. 65, pp. 1158-1174).

As a process for synthesizing tertiary phosphine compounds with, as an attached bulky hydrocarbon group, an attached tert-butyl group, a process comprising reacting di-tert-butylphosphinous chloride with a lithium reagent of alkyl or aryl or a Grignard reagent of alkyl or aryl has been heretofore known, as shown in the following examples (1) to (9).

Especially when a tertiary alkyl group is introduced into di-tert-butylphosphinous chloride, only an alkyllithium reagent is employed as shown in the process described in the following document (1), because an alkyl Grignard reagent suffers large steric hindrance and therefore has low reactivity.

(1) In "Chemische Berichte" (Germany), 1967, vol. 100, p. 693, it is described that tri-tert-butylphosphine is obtained in a yield of 50% by a process comprising reacting di-tert-butylphosphinous chloride with tert-butyllithium in a benzene-pentane mixed solvent.

In this process, however, tert-butyllithium that is tertialy alkyllithium is used as a starting material, and in the preparation process and the handling thereof, there are problems such as the following problems (i) and (ii), so that this process cannot be said to be convenient as an industrial production process.

(i) For preparing tertiary alkyllithium, a highly active lithium fine dispersion must be formed at a high temperature (about 200° C.), and the fine dispersion must be reacted with a tertiary alkyl halide using a low-boiling hydrocarbon as a solvent in a stream of argon. Therefore, reaction in a special vessel is required, and sufficient attention is necessary for the reaction operation.

(ii) The tertiary alkyllithium thus formed is a highly dangerous reagent which undergoes spontaneous ignition when it comes into contact with air.

(2) In "Journal of the Chemical Society (C)" (United Kingdom), 1971, p. 1931, it is described that di-tert-butylphenylphosphine is obtained in a yield of 60% by a process comprising reacting di-tert-butylphosphinous chloride with a phenyllithium reagent in an ether solvent.

In this process, however, metallic lithium that is dangerous in handling or alkyllithium that is expensive must be used in order to synthesize an aryllithium reagent that is a starting material. In the industrial production, therefore, there are problems in respects of safety and cost.

(3) In the pamphlet of International Publication No. 99/9040, pp. 5-6, it is described that α,α'-bis(di-tert-butylphosphino)-o-xylene is obtained in a yield of 61.8% by a process comprising reacting a Grignard reagent, which has been prepared from α,α'-dichloro-o-xylene and magnesium in a tetrahydrofuran solvent, with di-tert-butylphosphinous chloride of 4 equivalents at 50° C. for 24 hours.

In this process, di-tert-butylphosphinous chloride in an amount of 4 equivalents to the Grignard reagent that is a starting material is necessary, but the yield of the aimed product is low, and in the industrial production, this process is disadvantageous in respect of cost.

(4) In "Chemische Berichte" (Germany), 1967, vol. 100, p. 693, it is described that di-tert-butylisopropylphosphine is obtained by a process comprising reacting a Grignard reagent, which has been prepared from isopropyl bromide and magnesium, with di-tert-butylphohsphinous chloride.

In this process, the reaction is not completed, and the aimed product is obtained only as a mixture with di-tert-butylphosphinous chloride that is a starting material.

(5) In "Bulletin of the Korean Chemical Society" (Korea), 1999, vol. 20, p. 601, it is described that 1-(di-tert-butylphosphinomethyl)-o-carborane is obtained in a yield of 39% by a process comprising reacting a Grignard reagent, which has been prepared from 1-(bromomethyl)-o-carborane and magnesium, with di-tert-butylphosphinous chloride in ether for 2 hours under reflux.

In this process, the aimed product is obtained only in a low yield.

(6) In "Journal of the American Chemical Society" (U.S.A.), 1999, vol. 121, p. 4373, it is described that 2-(di-tert-butylphosphino)biphenyl is obtained in a yield of 67% by a process comprising reacting a Grignard reagent, which has been prepared from 2-bromobiphenyl and magnesium in tetrahydrofuran, with copper(I) chloride of 1.05 mol times the amount of 2-bromobiphenyl and with di-tert-butylphosphinous chloride of 1.20 mol times the amount of 2-bromobiphenyl for 8 hours under reflux, adding hexane and ether at room temperature, then temporarily taking out a copper complex of the aimed product as a solid and treating the copper complex with a mixture solution of hexane, ethyl acetate and an ammonia aqueous solution.

In this process, copper(I) chloride of 1.05 mol times the amount of 2-bromophenyl is used, and after the reaction, the aimed product is temporarily taken out of the system as a solid copper complex, and in order to decompose the copper complex, the copper complex is treated with ammonia water that is highly poisonous and causes environmental pollution. In this process, therefore, the reaction operations are complicated, and there is a problem in respect of working safety. In addition, a large amount of waste liquor containing copper and ammonia is produced, so that this process is not favorable as an industrial production process.

(7) In U.S. Pat. No. 6,307,087, it is described in the working examples that di-tert-butylphosphinous chloride is reacted with an aryl Grignard reagent using copper(I) chloride in an amount almost equimolar with di-tert-butylphosphinous chloride, more specifically, 2-(di-tert-butylphosphino)-4'-trifluoromethyl-biphenyl is obtained in a yield of 31% by a process comprising adding di-tert-butylphosphinous chloride and copper(I) chloride of 0.91 mol time the amount of di-tert-butylphosphinous chloride to a Grignard reagent, which has been prepared from 2-bromo-4'-trifluoromethyl-biphenyl and magnesium, reacting them for 14 hours with heating, then filtering a suspension obtained by diluting the reaction mixture with ether, and treating the resulting solid with ethyl acetate and ammonia water.

In this process, the aimed product is obtained only in a low yield. Further, copper(I) chloride is used in an amount almost equimolar with di-tert-butylphosphinous chloride, and in order to liberate the aimed product from the copper complex, treatment with ammonia water is essential. Therefore, there are problems similar to those in the document (6).

(8) In "Advanced Synthesis & Catalysis" (Germany), 2001, No. 8, p. 793, it is described that 2-(di-tert-butylphosphino)-2'-dimethylamino-biphenyl is obtained in a yield of 47% by a process comprising adding copper(I) chloride (15% by mol based on di-tert-butylphosphinous chloride) to a Grignard reagent, which has been prepared from 2-bromo-N,N-dimethylaniline, 2-bromochlorobenzene and magnesium, mixing them, subsequently adding di-tert-butylphosphinous chloride, reacting them at 60° C. for 20 hours, then adding an organic solvent and ammonia water and filtering the resulting reaction solution through Celite.

In this process, the amount of the copper compound used is decreased as compared with that in the document (6), and post treatment is carried out without taking out a copper complex of the aimed product from the reaction solution, but the yield is low. In addition, a problem of use of ammonia water has not been solved.

(9) In the pamphlet of International Publication No. 02/48160, p 17, it is described that di-tert-butyl(1-adamantyl)phosphine is obtained in a yield of 86% by a process comprising adding a 1-adamantylmagnesium bromide solution to a solution obtained by adding di-tert-butylphosphinous chloride, copper(I) iodide of 10% by mol and lithium bromide of 20% by mol based on the di-tert-butylphosphinous chloride to a solvent, reacting them at room temperature for 17 hours and filtering a solution obtained by solvent replacement of the reaction solution with benzene, through Celite.

In this process, the Grignard reagent is used in an amount of 2 mol times the amount of the di-tert-butylphosphinous chloride. Moreover, lithium bromide is used in addition to the copper compound, and after the reaction, it is necessary to perform solvent replacement with benzene that is carcinogenic and to perform filtration using Celite. Hence, there are problems in respects of economical efficiency, safety and workability.

Accordingly, any of the above processes is not industrially satisfactory.

Under such circumstances, development of a process for producing tertiary phosphine with an attached bulky hydrocarbon group such as a tert-butyl group or an adamantyl group in a high yield and with high purity on an industrial scale through simple and safe operations has been expected.

The present inventors have earnestly studied to solve the above problems, and as a result, they have found that tertiary phosphine can be produced in a high yield and with high purity by allowing a dialkylphosphinous halide having a tertiary hydrocarbon group to react with a Grignard reagent in the presence of a specific amount of a copper compound. Based on the finding, the present invention has been accomplished.

It is an object of the present invention to produce tertiary phopsphine with an attached sterically bulky hydrocarbon group, which is useful as a ligand of a transition metal catalyst in organic synthesis reactions, in a high yield and with high purity on an industrial scale through simple and safe operations.

SUMMARY OF THE INVENTION

The present invention is a process for producing tertiary phosphine represented by the following formula (3), comprising allowing a dialkylphosphinous halide represented by the following formula (1) to react with a Grignard reagent represented by the following formula (2) in the presence of a copper compound in an amount corresponding to 0.1 to 5% by mol based on the dialkylphosphinous halide represented by the formula (1);

wherein $R_1$, and $R_2$ are each independently a tertiary hydrocarbon group of 4 to 13 carbon atoms, and X is a chlorine atom or a bromine atom;

wherein $R_3$ is a straight-chain or branched alkyl group, an alkenyl group, an alkynyl group, a cycloalkyl group, an aralkyl group, a lower alkoxy lower alkyl group or an aryl group, and X' is a chlorine atom, a bromine atom or an iodine atom;

wherein $R_1$, $R_2$ and $R_3$ have the same meanings as defined above.

In the above process for producing tertiary phosphine, the first invention is characterized in that the dialkylphosphinous halide represented by the formula (1) is allowed to react with the Grignard reagent represented by the formula (2) wherein $R_3$ is an aryl group. In the first invention, the reaction is preferably carried out in the presence of a copper compound in an amount corresponding to 0.1 to 3% by mol based on the dialkylphosphinous halide represented by the formula (1).

In the process for producing tertiary phosphine, the second invention is characterized in that the dialkylphosphinous halide represented by the formula (1) is allowed to react with the Grignard reagent represented by the formula (2) wherein $R_3$ is a straight-chain or branched alkyl group, an alkenyl group, an alkynyl group, a cycloalkyl group, an aralkyl group or a lower alkoxy lower alkyl group. In the second invention, the reaction is preferably carried out in the presence of a copper compound in an amount corresponding to 0.1 to 3% by mol based on the dialkylphosphinous halide represented by the formula (1).

In the first and the second inventions, any of an inorganic copper compound and an organic copper compound is employable as the copper compound to be added, and particularly preferable is a copper halide or copper(II) acetylacetonate.

In the first and the second inventions, it is possible that a reaction mixture solution (a) of the dialkylphosphinous halide represented by the formula (1) and the Grignard reagent, water or an acid aqueous solution, and optionally, an appropriate organic solvent are mixed with stirring, then from the resulting mixture solution (b) an aqueous layer is removed by liquid separation, and thereafter the solvent is distilled off at atmospheric pressure or under reduced pressure, whereby the aimed tertiary phosphine can be produced in a high yield and with high purity through simple and safe operations.

That is to say, in the process of the invention, the dialkylphosphinous halide represented by the formula (1) is allowed to react with the Grignard reagent represented by the formula (2) using a copper compound as a catalyst, whereby the reaction readily proceeds without side reaction. Further, because the amount of the copper compound used is extremely small, a complex of the tertiary phosphine produced and the copper compound is formed in an extremely small amount. Therefore, an operation to liberate the aimed tertiary phosphine compound, such as treatment with ammonia water, is unnecessary, and the post treatment has only to be carried out in accordance with an ordinary process for synthesizing tertiary phosphine using a phosphinous halide and a Grignard reagent. In other words, in order to remove an inorganic salt formed as a by-product, such as a magnesium halide, treatment with a proper amount of water or an acid aqueous solution such as dilute sulfuric acid has only to be carried out, whereby the aimed tertiary phosphine can be obtained. Furthermore, because the amount of the copper compound used is much smaller than that in the conventional process, the amount of copper contained in the waste liquor is extremely small, and therefore, any special post treatment becomes unnecessary. Accordingly, the process of the invention is particularly suitable for the production of tertiary phosphine on an industrial scale.

DETAILED DESCRIPTION OF THE INVENTION

The dialkylphosphinous halide represented by the formula (1) that is a starting material can be synthesized by a publicly known process or in accordance with a publicly known process. For example, di-tert-butylphosphinous chloride as an example of dialkylphosphinous chloride can be synthesized by the process described in "Chemische Berichte" 1967, vol. 100, p. 692, and di-tert-amylphosphinous chloride as another example of dialkylphosphinous chloride can be synthesized by the process described in "Journal of the Chemical Society (C)" 1970, p. 2529, using phosphorus trichloride and the corresponding alkylmagnesium halide. Further, di-tert-butylphosphinous bromide as an example of dialkylphosphinous bromide can be synthesized by the process described in "Chemische Berichte" 1978, vol. 111, p. 1420, using phosphorus tribromide and the corresponding tert-butylmagnesium halide.

Examples of the dialkylphosphinous halides represented by the formula (1) include di-tert-butylphosphinous chloride, di-tert-butylphosphinous bromide, di-tert-amylphosphinous chloride, di-tert-amylphosphinous bromide, tert-amyl-tert-butylphosphinous chloride, bis(1,1-dimethylbutyl)phosphinous chloride, bis(1,1-diethylpropyl) phosphinous chloride, di(1-adamantyl)phosphinous chloride, di (1-adamantyl) phosphinous bromide and (1-adamantyl)-tert-butylphosphinous chloride.

The Grignard reagent that is the other starting material is represented by the formula (2). In the first invention, of the Grignard reagents represented by the formula (2), a compound wherein $R_3$ is an aryl group is allowed to react with the dialkylphosphinous halide represented by the formula (1). This aryl group is a phenyl group or a naphthyl group, and these groups may be substituted with a lower alkyl group, a lower alkoxy group, a di(lower alkyl)amino group, a phenyl group or a naphthyl group. Of these groups, the phenyl group and the naphthyl group may be further substituted with a lower alkyl group, a lower alkoxy group, a di(lower alkyl)amino group, a substituted phenyl group or a substituted naphthyl group.

Examples of the aryl groups indicated by $R_3$ include phenyl, 2-methylphenyl, 3-methylphenyl, 4-methylphenyl, 2-ethylphenyl, 4-ethylphenyl, 4-propylphenyl, 2-isopropylphenyl, 3-cyclopropylphenyl, 3-butylphenyl, 4-sec-butylphenyl, 4-tert-butylphenyl, 2-cyclohexylphenyl, 3-vinylphenyl, 4-vinylphenyl, 4-(2-propenyl)phenyl, 2-methoxyphenyl, 3-methoxyphenyl, 4-ethoxyphenyl, 4-isopropyloxyphenyl, 4-butyloxyphenyl, 4-tert-butyloxyphenyl, 4-tert-amyloxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, 2-methyl-4-methoxyphenyl, 4-dimethylaminophenyl, 2-phenylphenyl, 3-phenylphenyl, 4-phenylphenyl, 2-(2-methylphenyl)phenyl, 2-(2-isopropylphenyl) phenyl, 2-(4-tert-butylphenyl)phenyl, 2-(2-methoxyphenyl) phenyl, 2-(2-dimethylaminophenyl)phenyl, 2-(2-phenylphenyl)phenyl, 2-(1-naphthyl)phenyl, 2-(1-(2-methylphenyl)naphthyl, 1-naphthyl, 2-naphthyl, 2-(1-phenyl)naphthyl, 1-(2-(2-methylphenyl))naphthyl, 2-(1-(2-methylphenyl)naphthyl, 2-(1-(2-methoxyphenyl))naphthyl, 2-(1-(1-naphthyl))naphthyl, 1-(2-(1-(2-methyl)naphthyl)) naphthyl and 2-(1-(1-(2-methyl)naphthyl))naphthyl.

In the formula (2), X' is a chlorine atom, a bromine atom or an iodine atom.

In the second invention, of the Grignard reagents represented by the formula (2), a compound wherein $R_3$ is a straight-chain or branched alkyl group, an alkenyl group, an alkynyl group, a cycloalkyl group, an aralkyl group or a lower alkoxy lower alkyl group is allowed to react with the dialkylphosphinous halide represented by the formula (1). Examples of such groups indicated by $R_3$ include methyl, ethyl, n-propyl, isopropyl, n-butyl, sec-butyl, isobutyl, tert-butyl, n-pentyl, isoamyl, sec-amyl, tert-amyl, n-hexyl, 2-hexyl, 3-hexyl, n-heptyl, n-octyl, cyclopropyl, cyclopentyl, cyclohexyl, 1-adamantyl, 2-adamantyl, vinyl, allyl, 1-propenyl, 1-methylvinyl, 2-butenyl, ethynyl, 2-methoxyethyl, 2-phenoxyethyl, benzyl, α-methylbenzyl, p-methylbenzyl, o-methoxybenzyl, 2,4-dimethylbenzyl, phenethyl, p-methoxyphenethyl, p-(tert-butyloxy)phenethyl, 3-phenylpropyl, triphenylmethyl, diphenylmethyl, 2-phenyl-2-propyl, 1-phenyl-2-propyl, 1-naphthylmethyl and methoxymethyl.

In the formula (2), X' is a chlorine atom, a bromine atom or an iodine atom.

The Grignard reagent represented by the formula (2) can be prepared by an ordinary process for preparing a Grignard reagent, that is, by allowing a halogenated hydrocarbon ($R_3X'$) corresponding to the formula (2) to react with metallic magnesium in an ether solvent or a mixed solvent of an ether solvent and a hydrocarbon solvent.

Examples of the ether solvents used in the above reaction include chain ethers, such as diethyl ether, dipropyl ether, diisopropyl ether, dibutyl ether, diisoamyl ether, tert-butyl methyl ether, 1,2-dimethoxyethane and 1,2-diethoxyethane, and cyclic ethers, such as tetrahydrofuran, 2-methyltetrahydrofuran, tetrahydropyran and 1,4-dioxane. These ether solvents may be used singly or in combination of two or more kinds.

Examples of the hydrocarbon solvents include aliphatic hydrocarbons, such as pentane, hexane, cyclohexane, heptane and octane, and aromatic hydrocarbons, such as benzene, toluene, o-xylene, m-xylene, p-xylene and ethylbenzene. These hydrocarbon solvents may be used singly or in combination of two or more kinds.

In the present invention, the Grignard reagent obtained by the above preparation process can be used as it is, in the form of an inert solvent solution, without being isolated, for the reaction with the dialkylphosphinous halide represented by the formula (1).

In the first and the second inventions, the reaction of the dialkylphosphinous halide of the formula (1) with the Grignard reagent of the formula (2) is carried out in an inert solvent. The inert solvent used for dissolving the dialkylphosphinous halide of the formula (1) is not specifically restricted, provided that it is inert to the starting materials for the reaction and the reaction product. Examples of such inert solvents include hydrocarbon solvents, such as toluene, xylene, hexane and heptane, ether solvents, such as diethyl ether and tetrahydrofuran, and mixed solvents thereof.

The amount of the Grignard reagent of the formula (2) used in the first invention is in the range of 0.5 to 5 equivalents, preferably 0.9 to 1.5 equivalents, to the dialkylphosphinous halide of the formula (1).

The amount of the Grignard reagent of the formula (2) used in the second invention is in the range of 0.5 to 5 equivalents to the dialkylphosphinous halide of the formula (1). Especially when the Grignard reagent of the formula (2) is a lower alkyl Grignard reagent (straight-chain or branched alkyl group of 1 to 4 carbon atoms), the unreacted Grignard reagent remaining is decomposed by the contact with water or an acid aqueous solution in the post treatment and becomes a combustible gas (e.g., methane, ethane or propane). Therefore, from the viewpoint of industrially carrying out the method of the invention as safe as possible, the amount of the Grignard reagent of the formula (2) is in the range of 0.9 to 1.5 equivalents to the dialkylphosphinous halide of the formula (1).

As the copper compound for use in the first and the second inventions, an inorganic copper compound or an organic copper compound is employable. Examples of the inorganic copper compounds include copper(I) chloride, copper(II) chloride, copper(I) bromide, copper(II) bromide, copper(I) iodide, copper(I) oxide, copper(II) oxide, copper(I) carbonate, copper(II) carbonate, copper(II) sulfate, copper(II) cyanide, copper(II) hydroxide and diammonium copper(II) chloride.

Examples of the organic copper compounds include copper(II) acetic anhydride, copper(II) acetate, copper(II) acetylacetonate, copper(II) benzoate, copper(II) benzoylacetonate, copper(II) citrate, copper(II) dipivaloylmethanate, copper(II) ethylacetoacetate, copper(II) 2-ethylhexanate, copper(II) oleate, copper(II) stearate, copper(I) thiocyanate and copper(II) trifluoroacetylacetonate.

Of the above copper compounds, a copper halide compound, such as copper(I) bromide, copper(II) bromide, copper(I) chloride or copper(II) chloride, or copper(II) acetylacetonate is preferably employed.

In the present invention, the copper compound is used in an amount of 0.1 to 5% by mol based on the dialkylphosphinous halide of the formula (1). By the use of the copper compound in this amount, tertiary phosphine of the formula (3) that is an aimed compound can be efficiently obtained in a particularly high yield.

If the amount of the copper compound used is less than 0.1% by mol based on the dialkylphosphinous halide of the formula (1), the reaction rate is slow, and the catalyst is deactivated in the course of the reaction. Therefore, the reaction does not proceed sufficiently, and the yield is lowered.

If the amount of the copper compound used exceeds 5% by mol, lowering of yield takes place for the following reasons though the reaction proceeds sufficiently. It is known that tertiary phosphine is coordinated to a copper compound to form a complex. For example, in "Inorganic Synthesis" 1979, p. 87, it is described that copper(I) chloride forms a complex together with triphenylphosphine in an amount of 3 mol times the copper(I) chloride. If the amount of the copper compound used is increased, the amount of the formed complex of the copper compound and the aimed phosphine compound is increased, and this causes lowering of yield. Moreover, in order to decompose the thus formed complex to liberate the aimed phosphine compound, treatment with ammonia or the like is necessary, and when the treatment is industrially carried out, a problem of heavy burden on the environment by waste liquor produced is brought about. In the present invention, however, the aimed tertiary phosphine can be produced in a sufficiently high yield even if the treatment with ammonia is not carried out.

Taking into account the reaction rate, yield, workability of the post treatment, etc., the amount of the copper compound used is particularly preferably in the range of 0.1 to 3% by mol based on the dialkylphosphinous halide of the formula (1).

The reaction in the invention generally proceeds at a temperature between $-70°$ C. and the boiling point of the solvent used, though it varies depending upon the types of the compounds of the formula (1) and the formula (2) used. The reaction temperature, however, is preferably between $20°$ C. and the boiling point of the solvent used. Although the reaction time varies depending upon the types of the compounds of the formula (1) and the formula (2) used, the type or the amount of the copper compound, the reaction temperature and the solvent used, it is in the range of 1 hour to 1 day, and in many cases, the reaction is completed in 2 to 5 hours.

The order of addition and the way of addition of the dialkylphosphinous halide of the formula (1), the Grignard reagent of the formula (2) and the copper compound are, for example, as follows. The Grignard reagent of the formula (2) and the copper compound are mixed in the aforesaid appropriate solvent, and to the mixture, the dialkylphosphinous halide of the formula (1) is added without a solvent, or a solution of the dialkylphosphinous halide of the formula (1) in the aforesaid appropriate solvent is added; or the dialkylphosphinous halide of the formula (1) and the copper compound are mixed in the aforesaid appropriate solvent, and to the mixture, the Grignard reagent of the formula (2) is added; or the dialkylphosphinous halide of the formula (1) and the copper compound are mixed in the aforesaid appropriate solvent, and the mixture is added to the Grignard reagent of the formula (2). The present invention, however, is not limited to these methods.

The treatment after the completion of the reaction in the first and the second inventions has only to be carried out in accordance with an ordinary process for synthesizing tertiary phosphine compounds using a dialkylphosphinous halide and a Grignard reagent. That is to say, in order to remove an inorganic salt formed as a by-product, such as a magnesium halide, a reaction mixture solution (a) of the dialkylphosphinous halide represented by the formula (1) and the Grignard reagent represented by the formula (2), a proper amount of water or an acid aqueous solution, and optionally, an appropriate organic solvent such as toluene are mixed to obtain a mixture solution (b), then from the mixture solution (b) an aqueous layer is removed by liquid separation, and thereafter the solvent is distilled off from the resulting organic layer at atmospheric pressure or under reduced pressure, whereby the aimed tertiary phosphine of the formula (3) can be obtained.

It is also possible that the organic solvent is added to the resulting reaction mixture solution (a) and mixed therewith, and then water or the acid aqueous solution is added to the resulting mixture and mixed therewith, or the reaction mixture solution (a) is added to the organic solvent and mixed therewith, and then the resulting solution is added to water or the acid aqueous solution and mixed therewith. The mixing method is not specifically restricted.

The tertiary phosphine obtained by the above process may be purified by distillation, recrystallization or the like, when needed, whereby a product of higher purity can be obtained.

Examples of the tertiary phosphine produced by the first invention are set forth in Table 1 to Table 4.

TABLE 1

| $R_1$ | $R_2$ | $R_3$ |
|---|---|---|
| tert-butyl | tert-butyl | phenyl |
| tert-butyl | tert-butyl | 2-methylphenyl |
| tert-butyl | tert-butyl | 3-methylphenyl |
| tert-butyl | tert-butyl | 4-methylphenyl |
| tert-butyl | tert-butyl | 2-ethylphenyl |
| tert-butyl | tert-butyl | 4-propylphenyl |
| tert-butyl | tert-butyl | 2-isopropylphenyl |
| tert-butyl | tert-butyl | 3-cyclopropylphenyl |
| tert-butyl | tert-butyl | 3-butylphenyl |
| tert-butyl | tert-butyl | 4-sec-butylphenyl |
| tert-butyl | tert-butyl | 2-cyclohexylphenyl |
| tert-butyl | tert-butyl | 3-vinylphenyl |
| tert-butyl | tert-butyl | 4-vinylphenyl |
| tert-butyl | tert-butyl | 4-(2-propenyl)phenyl |
| tert-butyl | tert-butyl | 2-methoxyphenyl |
| tert-butyl | tert-butyl | 3-methoxyphenyl |
| tert-butyl | tert-butyl | 4-methoxyphenyl |
| tert-butyl | tert-butyl | 4-ethoxyphenyl |
| tert-butyl | tert-butyl | 4-isopropyloxyphenyl |
| tert-butyl | tert-butyl | 4-butyloxyphenyl |
| tert-butyl | tert-butyl | 4-tert-butoxyphenyl |
| tert-butyl | tert-butyl | 4-tert-amyloxyphenyl |
| tert-butyl | tert-butyl | 2,3-dimethylphenyl |
| tert-butyl | tert-butyl | 2,4-dimethylphenyl |
| tert-butyl | tert-butyl | 2,5-dimethylphenyl |
| tert-butyl | tert-butyl | 2,6-dimethylphenyl |
| tert-butyl | tert-butyl | 3,4-dimethylphenyl |
| tert-butyl | tert-butyl | 3,5-dimethylphenyl |
| tert-butyl | tert-butyl | 2,4,6-trimethylphenyl |
| tert-butyl | tert-butyl | 2-methyl-4-methoxyphenyl |
| tert-butyl | tert-butyl | 2-phenylphenyl |
| tert-butyl | tert-butyl | 3-phenylphenyl |
| tert-butyl | tert-butyl | 4-phenylphenyl |
| tert-butyl | tert-butyl | 2-(2-methylphenyl)phenyl |
| tert-butyl | tert-butyl | 2-(2-isopropylphenyl)phenyl |
| tert-butyl | tert-butyl | 2-(4-tert-butylphenyl)phenyl |
| tert-butyl | tert-butyl | 2-(2-methoxyphenyl)phenyl |
| tert-butyl | tert-butyl | 2-(2-dimethylaminophenyl)phenyl |
| tert-butyl | tert-butyl | 2-(2-phenylphenyl)phenyl |
| tert-butyl | tert-butyl | 2-(1-naphthyl)phenyl |
| tert-butyl | tert-butyl | 1-naphthyl |
| tert-butyl | tert-butyl | 2-naphthyl |
| tert-butyl | tert-butyl | 2-(1-(2-methylphenyl))naphthyl |
| tert-butyl | tert-butyl | 2-(1-(2-methoxyphenyl))naphthyl |
| tert-butyl | tert-butyl | 2-(1-(1-naphthyl))naphthyl |

TABLE 1-continued

| $R_1$ | $R_2$ | $R_3$ |
|---|---|---|
| tert-butyl | tert-butyl | 2-(1-phenyl)naphthyl |
| tert-butyl | tert-butyl | 2-(1-(1-(2-methyl)naphthyl))naphthyl |

TABLE 2

| $R_1$ | $R_2$ | $R_3$ |
|---|---|---|
| tert-amyl | tert-amyl | phenyl |
| tert-amyl | tert-amyl | 2-methylphenyl |
| tert-amyl | tert-amyl | 3-methylphenyl |
| tert-amyl | tert-amyl | 4-methylphenyl |
| tert-amyl | tert-amyl | 2-ethylphenyl |
| tert-amyl | tert-amyl | 4-propylphenyl |
| tert-amyl | tert-amyl | 2-isopropylphenyl |
| tert-amyl | tert-amyl | 3-cyclopropylphenyl |
| tert-amyl | tert-amyl | 3-butylphenyl |
| tert-amyl | tert-amyl | 4-sec-butylphenyl |
| tert-amyl | tert-amyl | 4-cyclohexylphenyl |
| tert-amyl | tert-amyl | 3-vinylphenyl |
| tert-amyl | tert-amyl | 4-vinylphenyl |
| tert-amyl | tert-amyl | 4-(2-propenyl)phenyl |
| tert-amyl | tert-amyl | 2-methoxyphenyl |
| tert-amyl | tert-amyl | 3-methoxyphenyl |
| tert-amyl | tert-amyl | 4-methoxyphenyl |
| tert-amyl | tert-amyl | 4-ethoxyphenyl |
| tert-amyl | tert-amyl | 4-isopropyloxyphenyl |
| tert-amyl | tert-amyl | 4-butyloxyphenyl |
| tert-amyl | tert-amyl | 4-tert-butoxyphenyl |
| tert-amyl | tert-amyl | 4-tert-amyloxyphenyl |
| tert-amyl | tert-amyl | 2,3-dimethylphenyl |
| tert-amyl | tert-amyl | 2,4-dimethylphenyl |
| tert-amyl | tert-amyl | 2,5-dimethylphenyl |
| tert-amyl | tert-amyl | 2,6-dimethylphenyl |
| tert-amyl | tert-amyl | 3,4-dimethylphenyl |
| tert-amyl | tert-amyl | 3,5-dimethylphenyl |
| tert-amyl | tert-amyl | 2,4,6-trimethylphenyl |
| tert-amyl | tert-amyl | 2-methyl-4-methoxyphenyl |
| tert-amyl | tert-amyl | 2-phenylphenyl |
| tert-amyl | tert-amyl | 3-phenylphenyl |
| tert-amyl | tert-amyl | 4-phenylphenyl |
| tert-amyl | tert-amyl | 2-(2-methylphenyl)phenyl |
| tert-amyl | tert-amyl | 2-(2-isopropylphenyl)phenyl |
| tert-amyl | tert-amyl | 2-(4-tert-butylphenyl)phenyl |
| tert-amyl | tert-amyl | 2-(2-methoxyphenyl)phenyl |
| tert-amyl | tert-amyl | 2-(2-dimethylaminophenyl)phenyl |
| tert-amyl | tert-amyl | 2-(2-phenylphenyl)phenyl |
| tert-amyl | tert-amyl | 2-(1-naphthyl)phenyl |
| tert-amyl | tert-amyl | 1-naphthyl |
| tert-amyl | tert-amyl | 2-naphthyl |
| tert-amyl | tert-amyl | 2-(1-(2-methylphenyl))naphthyl |
| tert-butyl | tert-amyl | 2-(1-(2-methoxyphenyl))naphthyl |
| tert-amyl | tert-amyl | 2-(1-(1-naphthyl))naphthyl |
| tert-amyl | tert-amyl | 2-(1-phenyl)naphthyl |
| tert-amyl | tert-amyl | 2-(1-(1-(2-methyl)naphthyl))naphthyl |

TABLE 3

| $R_1$ | $R_2$ | $R_3$ |
|---|---|---|
| tert-butyl | tert-amyl | phenyl |
| tert-butyl | tert-amyl | 2-methylphenyl |
| tert-butyl | tert-amyl | 4-methylphenyl |
| tert-butyl | tert-amyl | 2-methoxyphenyl |
| tert-butyl | tert-amyl | 2,4-dimethylphenyl |
| tert-butyl | tert-amyl | 2,6-dimethylphenyl |
| tert-butyl | tert-amyl | 3,4-dimethylphenyl |
| tert-butyl | tert-amyl | 3,5-dimethylphenyl |
| tert-butyl | tert-amyl | 2,4,6-trimethylphenyl |
| tert-butyl | tert-amyl | 2-phenylphenyl |
| tert-butyl | tert-amyl | 4-phenylphenyl |

TABLE 3-continued

| R₁ | R₂ | R₃ |
|---|---|---|
| tert-butyl | tert-amyl | 2-(2-methylphenyl)phenyl |
| tert-butyl | tert-amyl | 2-(2-methoxyphenyl)phenyl |
| tert-butyl | tert-amyl | 2-(2-phenylphenyl)phenyl |
| tert-butyl | tert-amyl | 1-naphthyl |
| tert-butyl | tert-amyl | 2-naphthyl |
| tert-butyl | tert-amyl | 2-(1-(1-naphthyl))naphthyl |
| 1,1-dimethylbutyl | 1,1-dimethylbutyl | phenyl |
| 1,1-dimethylbutyl | 1,1-dimethylbutyl | 2-methylphenyl |
| 1,1-dimethylbutyl | 1,1-dimethylbutyl | 2-phenylphenyl |
| 1,1-dimethylbutyl | 1,1-dimethylbutyl | 2-(1-naphthyl)phenyl |
| 1,1-dimethylbutyl | 1,1-dimethylbutyl | 1-naphthyl |
| tert-butyl | 1-adamantyl | phenyl |
| tert-butyl | 1-adamantyl | 2-methylphenyl |
| tert-butyl | 1-adamantyl | 2-phenylphenyl |
| tert-butyl | 1-adamantyl | 2-(1-naphthyl)phenyl |
| tert-butyl | 1-adamantyl | 1-naphthyl |

TABLE 4

| R₁ | R₂ | R₃ |
|---|---|---|
| 1-adamantyl | 1-adamantyl | phenyl |
| 1-adamantyl | 1-adamantyl | 2-methylphenyl |
| 1-adamantyl | 1-adamantyl | 4-methylphenyl |
| 1-adamantyl | 1-adamantyl | 2-ethylphenyl |
| 1-adamantyl | 1-adamantyl | 2-isopropylphenyl |
| 1-adamantyl | 1-adamantyl | 3-cyclopropylphenyl |
| 1-adamantyl | 1-adamantyl | 4-sec-butylphenyl |
| 1-adamantyl | 1-adamantyl | 4-cyclohexylphenyl |
| 1-adamantyl | 1-adamantyl | 4-vinylphenyl |
| 1-adamantyl | 1-adamantyl | 2-methoxyphenyl |
| 1-adamantyl | 1-adamantyl | 3-methoxyphenyl |
| 1-adamantyl | 1-adamantyl | 4-ethoxyphenyl |
| 1-adamantyl | 1-adamantyl | 4-isopropyloxyphenyl |
| 1-adamantyl | 1-adamantyl | 4-tert-butoxyphenyl |
| 1-adamantyl | 1-adamantyl | 4-tert-amyloxyphenyl |
| 1-adamantyl | 1-adamantyl | 2,4-dimethylphenyl |
| 1-adamantyl | 1-adamantyl | 2,5-dimethylphenyl |
| 1-adamantyl | 1-adamantyl | 2,6-dimethylphenyl |
| 1-adamantyl | 1-adamantyl | 3,5-dimethylphenyl |
| 1-adamantyl | 1-adamantyl | 2,4,6-trimethylphenyl |
| 1-adamantyl | 1-adamantyl | 2-methyl-4-methoxyphenyl |
| 1-adamantyl | 1-adamantyl | 2-phenylphenyl |
| 1-adamantyl | 1-adamantyl | 3-phenylphenyl |
| 1-adamantyl | 1-adamantyl | 4-phenylphenyl |
| 1-adamantyl | 1-adamantyl | 2-(2-methylphenyl)phenyl |
| 1-adamantyl | 1-adamantyl | 2-(2-isopropylphenyl)phenyl |
| 1-adamantyl | 1-adamantyl | 2-(4-tert-butylphenyl)phenyl |
| 1-adamantyl | 1-adamantyl | 2-(2-methoxyphenyl)phenyl |
| 1-adamantyl | 1-adamantyl | 2-(2-phenylphenyl)phenyl |
| 1-adamantyl | 1-adamantyl | 2-(1-naphthyl)phenyl |
| 1-adamantyl | 1-adamantyl | 1-naphthyl |
| 1-adamantyl | 1-adamantyl | 2-naphthyl |
| 1-adamantyl | 1-adamantyl | 1-(2-(2-methylphenyl))naphthyl |
| 1-adamantyl | 1-adamantyl | 2-(1-(1-naphthyl))naphthyl |
| 1-adamantyl | 1-adamantyl | 2-(1-phenyl)naphthyl |
| 1-adamantyl | 1-adamantyl | 2-(1-(2-methyl)naphthyl))naphthyl |

Examples of the tertiary phosphine produced by the second invention are set forth in Table 5 to Table 9.

TABLE 5

| R₁ | R₂ | R₃ |
|---|---|---|
| tert-butyl | tert-butyl | methyl |
| tert-butyl | tert-butyl | ethyl |
| tert-butyl | tert-butyl | n-propyl |
| tert-butyl | tert-butyl | isopropyl |
| tert-butyl | tert-butyl | n-butyl |

TABLE 5-continued

| R₁ | R₂ | R₃ |
|---|---|---|
| tert-butyl | tert-butyl | sec-butyl |
| tert-butyl | tert-butyl | isobutyl |
| tert-butyl | tert-butyl | tert-butyl |
| tert-butyl | tert-butyl | n-pentyl |
| tert-butyl | tert-butyl | isoamyl |
| tert-butyl | tert-butyl | tert-amyl |
| tert-butyl | tert-butyl | n-hexyl |
| tert-butyl | tert-butyl | 1,1-dimethylbutyl |
| tert-butyl | tert-butyl | 1,2-dimethylbutyl |
| tert-butyl | tert-butyl | n-octyl |
| tert-butyl | tert-butyl | n-nonyl |
| tert-butyl | tert-butyl | n-decyl |
| tert-butyl | tert-butyl | n-undecyl |
| tert-butyl | tert-butyl | n-dodecyl |
| tert-butyl | tert-butyl | n-tridecyl |
| tert-butyl | tert-butyl | n-tetradecyl |
| tert-butyl | tert-butyl | n-pentadecyl |
| tert-butyl | tert-butyl | n-hexadecyl |
| tert-butyl | tert-butyl | n-heptadecyl |
| tert-butyl | tert-butyl | n-octadecyl |
| tert-butyl | tert-butyl | n-nonadecyl |
| tert-butyl | tert-butyl | n-eicosyl |
| tert-butyl | tert-butyl | vinyl |
| tert-butyl | tert-butyl | allyl |
| tert-butyl | tert-butyl | 1-propenyl |
| tert-butyl | tert-butyl | 3-butenyl |
| tert-butyl | tert-butyl | 2-propynyl |
| tert-butyl | tert-butyl | cyclopropyl |
| tert-butyl | tert-butyl | cyclopentyl |
| tert-butyl | tert-butyl | cyclohexyl |
| tert-butyl | tert-butyl | 1-methylcyclohexyl |
| tert-butyl | tert-butyl | benzyl |
| tert-butyl | tert-butyl | phenethyl |
| tert-butyl | tert-butyl | diphenylmethyl |
| tert-butyl | tert-butyl | triphenylmethyl |
| tert-butyl | tert-butyl | α-methylbenzyl |
| tert-butyl | tert-butyl | p-methylbenzyl |
| tert-butyl | tert-butyl | 3-phenylpropyl |
| tert-butyl | tert-butyl | 2-phenyl-2-propyl |
| tert-butyl | tert-butyl | p-methoxyphenethyl |
| tert-butyl | tert-butyl | 1-naphthylmethyl |
| tert-butyl | tert-butyl | 1-adamantyl |
| tert-butyl | tert-butyl | 2-adamantyl |

TABLE 6

| R₁ | R₂ | R₃ |
|---|---|---|
| tert-amyl | tert-amyl | methyl |
| tert-amyl | tert-amyl | ethyl |
| tert-amyl | tert-amyl | n-propyl |
| tert-amyl | tert-amyl | isopropyl |
| tert-amyl | tert-amyl | n-butyl |
| tert-amyl | tert-amyl | sec-butyl |
| tert-amyl | tert-amyl | isobutyl |
| tert-amyl | tert-amyl | tert-butyl |
| tert-amyl | tert-amyl | n-pentyl |
| tert-amyl | tert-amyl | isoamyl |
| tert-amyl | tert-amyl | tert-amyl |
| tert-amyl | tert-amyl | n-hexyl |
| tert-amyl | tert-amyl | 1,1-dimethylbutyl |
| tert-amyl | tert-amyl | 1,2-dimethylbutyl |
| tert-amyl | tert-amyl | n-octyl |
| tert-amyl | tert-amyl | n-nonyl |
| tert-amyl | tert-amyl | n-decyl |
| tert-amyl | tert-amyl | n-undecyl |
| tert-amyl | tert-amyl | n-dodecyl |
| tert-amyl | tert-amyl | n-tridecyl |
| tert-amyl | tert-amyl | n-tetradecyl |
| tert-amyl | tert-amyl | n-pentadecyl |
| tert-amyl | tert-amyl | n-hexadecyl |
| tert-amyl | tert-amyl | n-heptadecyl |
| tert-amyl | tert-amyl | n-octadecyl |
| tert-amyl | tert-amyl | n-nonadecyl |

TABLE 6-continued

| R₁ | R₂ | R₃ |
| --- | --- | --- |
| tert-amyl | tert-amyl | n-eicosyl |
| tert-amyl | tert-amyl | vinyl |
| tert-amyl | tert-amyl | allyl |
| tert-amyl | tert-amyl | 1-propenyl |
| tert-amyl | tert-amyl | 3-butenyl |
| tert-amyl | tert-amyl | 2-propynyl |
| tert-amyl | tert-amyl | cyclopropyl |
| tert-amyl | tert-amyl | cyclopentyl |
| tert-amyl | tert-amyl | cyclohexyl |
| tert-amyl | tert-amyl | 1-methylcyclohexyl |
| tert-amyl | tert-amyl | benzyl |
| tert-amyl | tert-amyl | phenethyl |
| tert-amyl | tert-amyl | diphenylmethyl |
| tert-amyl | tert-amyl | triphenylmethyl |
| tert-amyl | tert-amyl | α-methylbenzyl |
| tert amyl | tert-amyl | p-methylbenzyl |
| tert-butyl | tert-amyl | 3-phenylpropyl |
| tert-amyl | tert-amyl | 2-phenyl-2-propyl |
| tert-amyl | tert-amyl | p-methoxyphenethyl |
| tert-amyl | tert-amyl | 1-naphthylmethyl |
| tert-amyl | tert-amyl | 1-adamantyl |
| tert-amyl | tert-amyl | 2-adamantyl |

TABLE 7

| R₁ | R₂ | R₃ |
| --- | --- | --- |
| tert-butyl | tert-amyl | methyl |
| tert-butyl | tert-amyl | ethyl |
| tert-butyl | tert-amyl | isopropyl |
| tert-butyl | tert-amyl | n-butyl |
| tert-butyl | tert-amyl | tert-butyl |
| tert-butyl | tert-amyl | n-pentyl |
| tert-butyl | tert-amyl | tert-amyl |
| tert-butyl | tert-amyl | vinyl |
| tert-butyl | tert-amyl | allyl |
| tert-butyl | tert-amyl | 3-butenyl |
| tert-butyl | tert-amyl | cyclopentyl |
| tert-butyl | tert-amyl | cyclohexyl |
| tert-butyl | tert-amyl | benzyl |
| tert-butyl | tert-amyl | phenethyl |
| tert-butyl | tert-amyl | α-methylbenzyl |
| tert-butyl | tert-amyl | p-methylbenzyl |
| tert-butyl | tert-amyl | 2-phenyl-2-propyl |
| tert-butyl | tert-amyl | p-methoxyphenethyl |
| tert-butyl | tert-amyl | 1-naphthylmethyl |
| tert-butyl | tert-amyl | 1-adamantyl |
| 1,1-dimethylbutyl | 1,1-dimethylbutyl | methyl |
| 1,1-dimethylbutyl | 1,1-dimethylbutyl | ethyl |
| 1,1-dimethylbutyl | 1,1-dimethylbutyl | isopropyl |
| 1,1-dimethylbutyl | 1,1-dimethylbutyl | n-butyl |
| 1,1-dimethylbutyl | 1,1-dimethylbutyl | tert-butyl |
| 1,1-dimethylbutyl | 1,1-dimethylbutyl | n-pentyl |
| 1,1-dimethylbutyl | 1,1-dimethylbutyl | tert-amyl |
| 1,1-dimethylbutyl | 1,1-dimethylbutyl | vinyl |
| 1,1-dimethylbutyl | 1,1-dimethylbutyl | allyl |
| 1,1-dimethylbutyl | 1,1-dimethylbutyl | 3-butenyl |
| 1,1-dimethylbutyl | 1,1-dimethylbutyl | cyclopentyl |
| 1,1-dimethylbutyl | 1,1-dimethylbutyl | cyclohexyl |
| 1,1-dimethylbutyl | 1,1-dimethylbutyl | benzyl |
| 1,1-dimethylbutyl | 1,1-dimethylbutyl | phenethyl |
| 1,1-dimethylbutyl | 1,1-dimethylbutyl | α-methylbenzyl |
| 1,1-dimethylbutyl | 1,1-dimethylbutyl | p-methylbenzyl |
| 1,1-dimethylbutyl | 1,1-dimethylbutyl | 2-phenyl-2-propyl |
| 1,1-dimethylbutyl | 1,1-dimethylbutyl | p-methoxyphenethyl |
| 1,1-dimethylbutyl | 1,1-dimethylbutyl | 1-naphthylmethyl |
| 1,1-dimethylbutyl | 1,1-dimethylbutyl | 1-adamantyl |

TABLE 8

| R₁ | R₂ | R₃ |
| --- | --- | --- |
| tert-butyl | 1-adamantyl | methyl |
| tert-butyl | 1-adamantyl | ethyl |
| tert-butyl | 1-adamantyl | isopropyl |
| tert-butyl | 1-adamantyl | n-butyl |
| tert-butyl | 1-adamantyl | tert-butyl |
| tert-butyl | 1-adamantyl | n-pentyl |
| tert-butyl | 1-adamantyl | tert-amyl |
| tert-butyl | 1-adamantyl | vinyl |
| tert-butyl | 1-adamantyl | allyl |
| tert-butyl | 1-adamantyl | 3-butenyl |
| tert-butyl | 1-adamantyl | cyclopentyl |
| tert-butyl | 1-adamantyl | cyclohexyl |
| tert-butyl | 1-adamantyl | benzyl |
| tert-butyl | 1-adamantyl | phenethyl |
| tert-butyl | 1-adamantyl | α-methylbenzyl |
| tert-butyl | 1-adamantyl | p-methylbenzyl |
| tert-butyl | 1-adamantyl | 2-phenyl-2-propyl |
| tert-butyl | 1-adamantyl | p-methoxyphenethyl |
| tert-butyl | 1-adamantyl | 1-naphthylmethyl |
| tert-butyl | 1-adamantyl | 1-adamantyl |

TABLE 9

| R₁ | R₂ | R₃ |
| --- | --- | --- |
| 1-adamantyl | 1-adamantyl | methyl |
| 1-adamantyl | 1-adamantyl | Ethyl |
| 1-adamantyl | 1-adamantyl | n-propyl |
| 1-adamantyl | 1-adamantyl | isopropyl |
| 1-adamantyl | 1-adamantyl | n-butyl |
| 1-adamantyl | 1-adamantyl | sec-butyl |
| 1-adamantyl | 1-adamantyl | isobutyl |
| 1-adamantyl | 1-adamantyl | tert-butyl |
| 1-adamantyl | 1-adamantyl | n-pentyl |
| 1-adamantyl | 1-adamantyl | isoamyl |
| 1-adamantyl | 1-adamantyl | tert-amyl |
| 1-adamantyl | 1-adamantyl | n-hexyl |
| 1-adamantyl | 1-adamantyl | 1,1-dimethylbutyl |
| 1-adamantyl | 1-adamantyl | 1,2-dimethylbutyl |
| 1-adamantyl | 1-adamantyl | n-octyl |
| 1-adamantyl | 1-adamantyl | n-nonyl |
| 1-adamantyl | 1-adamantyl | n-decyl |
| 1-adamantyl | 1-adamantyl | n-undecyl |
| 1-adamantyl | 1-adamantyl | n-dodecyl |
| 1-adamantyl | 1-adamantyl | n-tridecyl |
| 1-adamantyl | 1-adamantyl | n-tetradecyl |
| 1-adamantyl | 1-adamantyl | n-pentadecyl |
| 1-adamantyl | 1-adamantyl | n-hexadecyl |
| 1-adamantyl | 1-adamantyl | n-heptadecyl |
| 1-adamantyl | 1-adamantyl | n-octadecyl |
| 1-adamantyl | 1-adamantyl | n-nonadecyl |
| 1-adamantyl | 1-adamantyl | n-eicosyl |
| 1-adamantyl | 1-adamantyl | vinyl |
| 1-adamantyl | 1-adamantyl | allyl |
| 1-adamantyl | 1-adamantyl | 1-propenyl |
| 1-adamantyl | 1-adamantyl | 3-butenyl |
| 1-adamantyl | 1-adamantyl | 2-propynyl |
| 1-adamantyl | 1-adamantyl | cyclopropyl |
| 1-adamantyl | 1-adamantyl | cyclopentyl |
| 1-adamantyl | 1-adamantyl | cyclohexyl |
| 1-adamantyl | 1-adamantyl | 1-methylcyclohexyl |
| 1-adamantyl | 1-adamantyl | benzyl |
| 1-adamantyl | 1-adamantyl | phenethyl |
| 1-adamantyl | 1-adamantyl | diphenylmethyl |
| 1-adamantyl | 1-adamantyl | triphenylmethyl |
| 1-adamantyl | 1-adamantyl | α-methylbenzyl |
| 1-adamantyl | 1-adamantyl | p-methylbenzyl |
| 1-adamantyl | 1-adamantyl | 3-phenylpropyl |
| 1-adamantyl | 1-adamantyl | 2-phenyl-2-propyl |
| 1-adamantyl | 1-adamantyl | p-methoxyphenethyl |
| 1-adamantyl | 1-adamantyl | 1-naphthylmethyl |
| 1-adamantyl | 1-adamantyl | 1-adamantyl |
| 1-adamantyl | 1-adamantyl | 2-adamantyl |

According to the present invention, tertiary phosphine with an attached sterically bulky hydrocarbon group, which is useful as a ligand of a transition metal catalyst in organic synthesis reactions, can be produced on an industrial scale through simple and safe operations, as described hereinbefore.

By the use of a copper compound in the catalytic amount, tertiary phosphine can be produced in a high yield and with high purity, and the amount of waste liquor produced in the post treatment after the reaction can be remarkably decreased.

Moreover, because a Grignard reagent which can be easily prepared industrially and has high reactivity is used as a starting material, tertiary phosphine having various bulky substituents can be produced.

EXAMPLES

The present invention of further described with reference to the following examples, but it be understood that the invention is in no way limited to or by those examples.

In the following examples, purity (%) is an area percentage value obtained by gas chromatography analysis. With regard to the amount of the copper compound added, "% by mol" based on the dialkylphosphinous chloride is also set forth.

Example 1

Synthesis (1) of di-tert-butylphenylphosphine

In a 300 ml four-necked flask thoroughly purged with nitrogen, 40 ml of tetrahydrofuran, 18.1 g (0.1 mol) of di-tert-butylphosphinous chloride and 0.14 g (0.001 mol (corresponding to 1% by mol)) of copper(I) bromide were placed. To the contents of the flask, a Grignard reagent solution previously prepared from 13.5 g (0.12 mol) of chlorobenzene and 3.5 g (0.14 mol) of metallic magnesium in 100 ml of tetrahydrofuran was dropwise added over a period of 1 hour with maintaining the temperature at 25° C. to 30° C. After the dropwise addition was completed, stirring was conducted at a temperature of 35° C. to 40° C. for 3 hours. After the temperature of the reaction solution was returned to room temperature, disappearance of di-tert-butylphosphinous chloride was confirmed by gas chromatography. Thereafter, 40 ml of toluene and 30 ml of a 5% sulfuric acid aqueous solution were added to the reaction solution to perform liquid separation. Then, the organic layer was washed with water and dried over anhydrous sodium sulfate. The solvent was distilled off under reduced pressure, followed by further distillation. Then, fractions given by distillation at 110° C. to 112° C. under reduced pressure of 5 Torr were collected. As a result, 19.9 g (purity: 99.0%) of the aimed di-tert-butylphenylphosphine was obtained as a viscous oily substance. The yield was 89.0%.

Example 2

Synthesis (2) of di-tert-butylphenylphosphine

The same operations as in Example 1 were carried out, except that 18.8 g (0.12 mol) of bromobenzene was used instead of chlorobenzene. As a result, 19.6 g (purity: 99.1%) of di-tert-butylphenylphosphine was obtained. The yield was 88.5%.

Example 3

Synthesis of di-tert-butyl(2-methylphenyl)phosphine

In a 500 ml four-necked flask thoroughly purged with nitrogen, a Grignard reagent solution previously prepared from 20.5 g (0.12 mol) of 2-bromotoluene and 3.1 g (0.13 mol) of metallic magnesium in a mixed solvent of 100 ml of tetrahydrofuran and 40 ml of toluene, and 0.05 g (0.0005 mol (corresponding to 0.5% by mol)) of copper(I) chloride were placed. To the contents of the flask, a solution of 18.1 g (0.10 mol) of di-tert-butylphosphinous chloride in 30 ml of tetrahydrofuran was dropwise added over a period of 1 hour with maintaining the temperature at 25° C. to 30° C. After the dropwise addition was completed, stirring was conducted at 50° C. for 4 hours. After the temperature of the reaction solution was returned to room temperature, disappearance of di-tert-butylphosphinous chloride was confirmed by gas chromatography. Thereafter, 30 ml of a 5% sulfuric acid aqueous solution was added to the reaction solution to perform liquid separation. Then, the organic layer was washed with water and dried over anhydrous sodium sulfate. The solvent was distilled off under reduced pressure, followed by further distillation. Then, fractions given by distillation at 112° C. to 114° C. under reduced pressure of 3 Torr were collected. As a result, 21.5 g (purity: 99.0%) of the aimed di-tert-butyl(2-methylphenyl)phosphine was obtained. The yield was 91.0%.

Example 4

Synthesis (2) of di-tert-butyl(2-methylphenyl)phosphine

The same operations as in Example 3 were carried out, except that the amount of copper(I) chloride added was changed to 0.02 g (0.0002 mol (corresponding to 0.2% by mol)) and the reaction was conducted at 50° C. for 12 hours. As a result, 20.0 g (purity: 98.8%) of di-tert-butyl(2-methylphenyl)phosphine was obtained. The yield was 84.0%.

Example 5

Synthesis of di-tert-butyl(2-methoxyphenyl)phosphine

In a 300 ml four-necked flask thoroughly purged with nitrogen, a Grignard reagent solution previously prepared from 12.1 g (0.065 mol) of 2-bromoanisole and 2.1 g (0.085 mol) of metallic magnesium in 65 ml of tetrahydrofuran, and 0.13 g (0.0010 mol (corresponding to 2% by mol)) of copper(II) chloride were placed. To the contents of the flask, 9.0 g (0.05 mol) of di-tert-butylphosphinous chloride was dropwise added as it is without being dissolved in a solvent, over a period of 1 hour with maintaining the temperature at 25° C. to 30° C. After the dropwise addition was completed, stirring was conducted at 50° C. for 3 hours. After the temperature of the reaction solution was returned to room temperature, gas chromatography analysis was carried out, and as a result, di-tert-butylphosphinous chloride was present in trace amounts. Thereafter, 65 ml of toluene and 50 ml of water were added to the reaction solution to perform liquid separation. Then, the organic layer was washed with water and dried over anhydrous sodium sulfate. The solvent and a low-boiling component were distilled off under reduced pressure to obtain 11.9 g (purity: 95.0%) of the aimed di-tert-butyl(2-methoxyphenyl)phosphine was obtained. The yield was 89.7%.

Mass (CI method) M/z: 253 (M$^+$+1: base).

Example 6

Synthesis of di-tert-butyl(2-phenylphenyl)phosphine

In a 500 ml four-necked flask thoroughly purged with nitrogen, 9.0 g (0.05 mol) of di-tert-butylphosphinous chloride, 0.07 g (0.0005 mol (corresponding to 1% by mol)) of copper(I) bromide and 50 ml of tetrahydrofuran were placed. To the contents of the flask, a Grignard reagent solution previously prepared from 14.0 g (0.060 mol) of 2-bromobiphenyl and 1.7 g (0.072 mol) of metallic magnesium in 100 ml of tetrahydrofuran was dropwise added over a period of 1 hour with maintaining the temperature at 30° C. to 35° C. After the dropwise addition was completed, stirring was conducted at a reflux temperature for 4 hours. After the temperature of the reaction solution was returned to room temperature, disappearance of di-tert-butylphosphinous chloride was confirmed by gas chromatography. Thereafter, 30 ml of toluene and 30 ml of a 5% sulfuric acid aqueous solution were added to the reaction solution to perform liquid separation. Then, the organic layer was washed with water and dried over anhydrous sodium sulfate. The solvent and a low-boiling component were distilled off under reduced pressure to obtain coarse crystals. The coarse crystals were recrystallized from MeOH to obtain 13.2 g (purity: 99.0%) of the aimed di-tert-butyl(2-phenylphenyl)phosphine. The yield was 87.5%. Melting point: 84-85° C.

Example 7

Synthesis of di-tert-butyl(2,4,6-trimethylphenyl)phosphine

In a 300 ml four-necked flask thoroughly purged with nitrogen, 20 ml of tetrahydrofuran, 9.0 g (0.05 mol) of di-tert-butylphosphinous chloride and 0.05 g (0.0005 mol (corresponding to 1% by mol)) of copper(I) chloride were placed. To the contents of the flask, a Grignard reagent solution previously prepared from 14.9 g (0.075 mol) of mesityl bromide and 2.2 g (0.090 mol) of metallic magnesium in 100 ml of tetrahydrofuran was dropwise added over a period of 1 hour at 50° C. After the dropwise addition was completed, stirring was conducted under reflux at 73° C. for 4 hours. After the temperature of the reaction solution was returned to room temperature, 40 ml of toluene and 30 ml of a 5% sulfuric acid aqueous solution were added to the reaction solution to perform liquid separation. Then, the organic layer was washed with water and dried over anhydrous sodium sulfate. After the solvent was distilled off under reduced pressure, a small amount of MeOH was added, and the whole system was cooled to −30° C. to precipitate solids. The solids were filtered off to obtain 11.9 g (purity: 97.5%) of the aimed di-tert-butyl(2,4,6-trimethylphenyl)phosphine as white solids. The yield was 88.0%. Melting point: 36-37° C.

Example 8

Synthesis of di-tert-butyl(1-naphthyl)phosphine

In a 500 ml four-necked flask thoroughly purged with nitrogen, 18.1 g (0.1 mol) of di-tert-butylphosphinous chloride, 0.20 g (0.002 mol (corresponding to 2% by mol)) of copper(I) chloride, 20 ml of tetrahydrofuran and 20 ml of toluene were placed. To the contents of the flask, a Grignard reagent solution previously prepared from 24.8 g (0.12 mol) of 1-bromonaphthalene and 3.5 g (0.14 mol) of metallic magnesium in 180 ml of tetrahydrofuran was dropwise added over a period of 1 hour with maintaining the temperature at 25° C. to 30° C. After the dropwise addition was completed, stirring was conducted at 65° C. for 3 hours. After the temperature of the reaction solution was returned to room temperature, disappearance of di-tert-butylphosphinous chloride was confirmed by gas chromatography. Thereafter, 30 ml of toluene and 30 ml of a 5% sulfuric acid aqueous solution were added to the reaction solution to perform liquid separation. Then, the organic layer was washed with water and dried over anhydrous sodium sulfate. The solvent was distilled off under reduced pressure to obtain an oily substance. The oily substance was recrystallized from 150 ml of methanol to obtain 23.6 g (purity: 98.5%) of the aimed di-tert-butyl(1-naphthyl)phosphine as white crystals. The yield was 85.4%. Melting point: 95-97° C.

Example 9

Synthesis of di-tert-amylphenylphosphine

In a 300 ml four-necked flask thoroughly purged with nitrogen, 20 ml of tetrahydrofuran, 10.4 g (0.050 mol) of di-tert-amylphosphinous chloride and 0.13 g (0.0005 mol (corresponding to 1% by mol)) of copper(II) acetylacetonate were placed. To the contents of the flask, a Grignard reagent solution previously prepared from 6.8 g (0.060 mol) of chlorobenzene and 1.9 g (0.080 mol) of metallic magnesium in 45 ml of tetrahydrofuran was dropwise added over a period of 1 hour with maintaining the temperature at 40° C. to 45° C. After the dropwise addition was completed, stirring was conducted at the same temperature for 3 hours. After the temperature of the reaction solution was returned to room temperature, gas chromatography analysis was carried out, and as a result, di-tert-amylphosphinous chloride was present in trace amounts. Thereafter, 20 ml of toluene and 20 ml of a 5% sulfuric acid aqueous solution were added to the reaction solution to perform liquid separation. Then, the organic layer was washed with water and dried over anhydrous sodium sulfate. The solvent and a low-boiling component were distilled off under reduced pressure to obtain 12.0 g (purity: 94.4%) of the aimed di-tert-amylphenylphosphine as a viscous oily substance. The yield was 90.5%.

Mass (CI method) M/z: 251 (M$^+$+1: base).

Comparative Example 1

The same operations as in Example 1 were carried out, except that the amount of copper(I) bromide added was changed to 2.8 mg (0.02 mmol (corresponding to 0.02% by mol)). As a result of gas chromatography analysis after 24 hours, conversion to di-tert-butylphenylphosphine was 11%.

Comparative Example 2

The same operations as in Example 1 were carried out, except that the amount of copper(I) bromide was changed to 2.2 g (0.015 mol (corresponding to 15% by mol)), and after the reaction and the treatment, a low-boiling component was distilled off under reduced pressure. As a result, 12.1 g of the aimed di-tert-butylphenylphosphine was obtained as a viscous oily substance. The yield was 52.0%. Purity: 95.0%.

Example 10

Synthesis of di-tert-butylethylphosphine

In a 300 ml four-necked flask thoroughly purged with nitrogen, 18.1 g (0.1 mol) of di-tert-butylphosphinous chloride, 0.28 g (0.002- mol (corresponding to 2% by mol)) of copper(I) bromide and 60 ml of tetrahydrofuran were placed. To the contents of the flask, 55 ml (0.11 mol) of a tetrahydrofuran solution of ethylmagnesium chloride having a concentration of 2 mol/liter was dropwise added over a period of 1 hour with maintaining the temperature at 25° C. to 30° C. After the dropwise addition was completed, stirring was conducted at the same temperature for 2 hours. After the temperature of the reaction solution was returned to room temperature, disappearance of di-tert-butylphosphinous chloride was confirmed by gas chromatography. Thereafter, 50 ml of toluene and 30 ml of a 5% sulfuric acid aqueous solution were added to the reaction solution to perform liquid separation. Then, the organic layer was washed with water and dried over anhydrous sodium sulfate. The solvent was distilled off under reduced pressure, followed by further distillation. Then, fractions given by distillation at 92° C. to 95° C. under reduced pressure of 20 Torr were collected. As a result, 15.7 g (purity: 98.0%) of the aimed di-tert-butylethylphosphine was obtained as an oily substance. The yield was 88.2%.

Example 11

Synthesis (1) of di-tert-butylmethylphosphine

In a 300 ml four-necked flask thoroughly purged with nitrogen, 9.0 g (0.05 mol) of di-tert-butylphosphinous chloride, 0.025 g (0.25 mol (corresponding to 0.5% by mol)) of copper(I) chloride and 30 ml of tetrahydrofuran were placed. To the contents of the flask, 55 ml (0.055 mol) of a tetrahydrofuran solution of methylmagnesium bromide having a concentration of 1 mol/liter was dropwise added over a period of 1 hour with maintaining the temperature at 25° C. to 30° C. After the dropwise addition was completed, stirring was conducted at the same temperature for 5 hours. Then, disappearance of di-tert-butylphosphinous chloride was confirmed by gas chromatography. Thereafter, 40 ml of toluene and 40 ml of water were added to the reaction solution to perform liquid separation. Then, the organic layer was washed with water and dried over anhydrous sodium sulfate. The solvent was distilled off under reduced pressure, followed by further distillation. Then, fractions given by distillation at 750° C. to 810° C. under reduced pressure of 20 Torr were collected. As a result, 7.4 g (purity: 98.7%) of the aimed di-tert-butylmethylphosphine was obtained as an oily substance. The yield was 91.1%.

Example 12

Synthesis (2) of di-tert-butylmethylphosphine

The same operations as in Example 11 were carried out, except that the amount of copper(I) chloride added was changed to 0.010 g (0.10 mmol (corresponding to 0.2% by mol) and the reaction was conducted at 400° C. for 10 hours. As a result, 7.1 g (purity: 98.0%) of the aimed di-tert-butylmethylphosphine was obtained as an oily substance. The yield was 86.6%.

Example 13

Synthesis of di-tert-butylisopropylphosphine

In a 300 ml four-necked flask thoroughly purged with nitrogen, 9.0 g (0.05 mol) of di-tert-butylphosphinous chloride, 0.05 g (0.001 mol (corresponding to 1% by mol)) of copper(I) chloride and 30 ml of tetrahydrofuran were placed. To the contents of the flask, a Grignard reagent solution previously prepared from 4.7 g (0.060 mol) of isopropyl chloride and 1.7 g (0.072 mol) of metallic magnesium in 50 ml of tetrahydrofuran was dropwise added over a period of 1 hour with maintaining the temperature at 25° C. to 30° C. After the dropwise addition was completed, stirring was conducted at the same temperature for 3 hours. After the temperature of the reaction solution was returned to room temperature, disappearance of di-tert-butylphosphinous chloride was confirmed by gas chromatography. Thereafter, 20 ml of toluene and 30 ml of a 5% sulfuric acid aqueous solution were added to the reaction solution to perform liquid separation. Then, the organic layer was washed with water and dried over anhydrous sodium sulfate. The solvent and a low-boiling component were distilled off under reduced pressure to obtain 8.2 g (purity: 95.0%) of the aimed di-tert-butylisopropylphosphine as an oily substance. The yield was 92.7%.

Example 14

Synthesis of di-tert-butyl(n-butyl)phosphine

In a 300 ml four-necked flask thoroughly purged with nitrogen, a Grignard reagent solution previously prepared from 5.6 g (0.060 mol) of n-butyl chloride and 1.7 g (0.072 mol) of metallic magnesium in 100 ml of tetrahydrofuran, and 0.13 g (0.0005 mol (corresponding to 1% by mol)) of copper(II) acetylacetonate were placed. To the contents of the flask, a solution of 9.0 g (0.05 mol) of di-tert-butylphosphinous chloride in 30 ml of tetrahydrofuran was dropwise added over a period of 1 hour with maintaining the temperature at 20° C. to 25° C. After the dropwise addition was completed, stirring was conducted at the same temperature for 2 hours. Thereafter, 30 ml of toluene and 20 ml of a 5% sulfuric acid aqueous solution were added to the reaction solution to perform liquid separation. Then, the organic layer was washed with water and dried over anhydrous sodium sulfate. The solvent was distilled off under reduced pressure, followed by further distillation. Then, fractions given by distillation at 111° C. under reduced pressure of 19 Torr were collected. As a result, 9.4 g (purity: 98.0%) of the aimed di-tert-butyl(n-butyl)phosphine was obtained. The yield was 91.1%.

Example 15

Synthesis of tri-tert-butylphosphine

In a 200 ml four-necked flask thoroughly purged with nitrogen, 9.0 g (0.05 mol) of di-tert-butylphosphinous chloride, 0.05 g (0.0005 mol (corresponding to 1% by mol)) of copper(I) chloride and 20 ml of tetrahydrofuran were placed. To the contents of the flask, a Grignard reagent solution previously prepared from 6.0 g (0.065. mol) of tert-butyl chloride and 1.9 g (0.078 mol) of metallic magnesium in 50 ml of tetrahydrofuran was dropwise added over a period of 1 hour with maintaining the temperature at 20° C. to 25° C.

After the dropwise addition was completed, stirring was conducted at a temperature of 35° C. to 40° C. for 3 hours. Then, disappearance of di-tert-butylphosphinous chloride was confirmed by gas chromatography. Thereafter, 20 ml of toluene and 20 ml of a 5% sulfuric acid aqueous solution were added to the reaction solution to perform liquid separation. Then, the organic layer was washed with water and dried over anhydrous sodium sulfate. The solvent was distilled off under reduced pressure, followed by further distillation. Then, fractions given by distillation at 111° C. to 113° C. under reduced pressure of 15 Torr were collected. As a result, 9.2 g (purity: 99.0%) of the aimed tri-tert-butylphosphine was obtained as an oily substance. The yield was 90.2%.

Example 16

Synthesis of di-tert-butylbenzylphosphine

In a 200 ml four-necked flask thoroughly purged with nitrogen, a Grignard reagent solution previously prepared from 8.2 g (0.065 mol) of benzyl chloride and 2.1 g (0.085 mol) of metallic magnesium in 50 ml of tetrahydrofuran, and 0.055 g (0.0003 mol (corresponding to 0.6% by mol)) of copper(II) bromide were placed. To the contents of the flask, 9.0 g (0.05 mol) of di-tert-butylphosphinous chloride was dropwise added as it is without being dissolved in a solvent, over a period of 1 hour at a temperature in the vicinity of 40° C. After the dropwise addition was completed, stirring was conducted at a temperature of 40° C. to 45° C. for 3 hours. After the temperature of the reaction solution was returned to room temperature, 20 ml of toluene and 20 ml of a 5% sulfuric acid aqueous solution were added to the reaction solution to perform liquid separation. Then, the organic layer was washed with water and dried over anhydrous sodium sulfate. The solvent was distilled off under reduced pressure, followed by further distillation. Then, fractions given by distillation at 145° C. to 150° C. under reduced pressure of 0.5 Torr were collected. As a result, 10.6 g (purity: 98.5%) of the aimed di-tert-butylbenzylphosphine was obtained as an oily substance. The yield was 88.3%.

Example 17

Synthesis of di-tert-amylcyclohexylphosphine

In a 300 ml four-necked flask thoroughly purged with nitrogen, 10.4 g (0.05 mol) of di-tert-amylphosphinous chloride, 0.10 g (0.001 mol (corresponding to 2% by mol)) of copper(I) chloride and 30 ml of tetrahydrofuran were placed. To the contents of the flask, a Grignard reagent solution previously prepared from 8.3 g (0.060 mol) of cyclohexyl chloride and 2.0 g (0.08 mol) of metallic magnesium in 50 ml of tetrahydrofuran was dropwise added over a period of 1 hour with maintaining the temperature at 25° C. to 30° C. After the dropwise addition was completed, stirring was conducted at a temperature of 35° C. to 40° C. for 6 hours. After the temperature of the reaction solution was returned to room temperature, 20 ml of toluene and 20 ml of a 5% sulfuric acid aqueous solution were added to the reaction solution to perform liquid separation. Then, the organic layer was washed with water and dried over anhydrous sodium sulfate. The solvent and a low-boiling component were distilled off under reduced pressure to obtain 12.4 g (purity: 94.9%) of the aimed di-tert-amylcyclohexylphosphine as an oily substance. The yield was 90.2%.

Mass (CI method) M/z: 257 (M$^+$+1: base).

Comparative Example 3

The same operations as in Example 15 were carried out, except that the amount of copper(I) chloride added was changed to 3 mg (corresponding to 0.05% by mol based on the di-tert-butylphosphinous chloride), and the reaction was conducted at a reflux temperature for 10 hours. As a result of gas chromatography analysis after the reaction, conversion to tri-tert-butylphosphine was 15%.

Comparative Example 4

The same operations as in Example 15 were carried out, except that the amount of copper(I) chloride added was changed to 0.75 g (corresponding to 15% by mol based on the di-tert-butylphosphinous chloride), and after the reaction and the treatment, the solvent and a low-boiling component were distilled off under reduced pressure. As a result, 5.9 g (purity: 93.8%) of tri-tert-butylphosphine was obtained as an oily substance. The yield was 54.4%.

What is claimed is:

1. A process for producing tertiary phosphine represented by the following formula (3), comprising allowing a dialkylphosphinous halide represented by the following formula (1) to react with a Grignard reagent represented by the following formula (2) in the presence of a copper compound in an amount corresponding to 0.1 to 5% by mol based on the dialkylphosphinous halide represented by the formula (1);

wherein $R_1$ and $R_2$ are each independently a tertiary hydrocarbon group of 4 to 13 carbon atoms, and X is a chlorine atom or a bromine atom;

wherein $R_3$ is a straight-chain or branched alkyl group, an alkenyl group, an alkynyl group, a cycloalkyl group, an aralkyl group, a lower alkoxy lower alkyl group, and X' is a chlorine atom, a bromine atom or an iodine atom;

wherein $R_1$, $R_2$ and $R_3$ have the same meanings as defined above.

2. The process for producing tertiary phosphine as claimed in claim 1, wherein the reaction is carried out in the presence of a copper compound in an amount corresponding to 0.1 to 3% by mol based on the dialkyiphosphinous halide represented by the formula (1).

3. The process for producing tertiary phosphine as claimed in claim 1, wherein the resulting reaction product of the dialkylphosphinous halide represented by the formula (1) and the Grignard reagent represented by the formula (2) are mixed with water or an acid aqueous solution, and optionally, an organic solvent with stirring; then the aqueous layer of resulting mixture solution is removed by liquid separation, and thereafter the remaining solvent is distilled off at atmospheric pressure or under reduced pressure.

4. The process for producing tertiary phosphine as claimed in claim 1, wherein a carbon atom attached to a magnesium atom of the Grignard reagent is primary carbon.

5. The process for producing tertiary phosphine as claimed in claim 1, wherein a carbon atom attached to a magnesium atom of the Grignard reagent is secondary carbon.

6. The process for producing tertiary phosphine as claimed in claim 1, wherein a carbon atom attached to a magnesium atom of the Grignard reagent is tertiary carbon.

7. The process for producing tertiary phosphine as claimed in claim 1, wherein the copper compound is a copper halide or copper(II) acetylacetonate.

8. The process for producing tertiary phosphine as claimed in claim 1, wherein X of the dialkyiphosphinous halide represented by the formula (1) is chlorine.

9. The process for producing tertiary phosphine as claimed in claim 8, wherein the dialkylphosphinous halide represented by the formula (1) is di-tert-butylphosphinous chloride or di-tert-amylphosphinous chloride.

10. The process for producing tertiary phosphine as claimed in claim 9, wherein the dialkylphosphinous halide represented by the formula (1) is di-tert-butylphosphinous chloride, and the Grignard reagent is a tert-butylmagnesium halide.

11. The process for producing tertiary phosphine as claimed in claim 2, wherein the dialkylphosphinous halide represented by the formula (1) and the Grignard reagent, water or an acid aqueous solution, and optionally, an organic solvent are mixed with stirring, then from the resulting mixture solution an aqueous layer is removed by liquid separation, and thereafter the solvent is distilled off at atmospheric pressure or under reduced pressure.

12. The process for producing tertiary phosphine as claimed in claim 2, wherein the copper compound is a copper halide or copper(II) acetylacetonate.

13. The process for producing tertiary phosphine as claimed in claim 2, wherein X of the dialkylphosphinous halide represented by the formula (1) is chlorine.

14. The process for producing tertiary phosphine as claimed in claim 2, wherein a carbon atom attached to a magnesium atom of the Grignard reagent is primary carbon.

15. The process for producing tertiary phosphine as claimed in claim 3, wherein a carbon atom attached to a magnesium atom of the Grignard reagent is primary carbon.

16. The process for producing tertiary phosphine as claimed in claim 2, wherein a carbon atom attached to a magnesium atom of the Grignard reagent is secondary carbon.

17. The process for producing tertiary phosphine as claimed in claim 3, wherein a carbon atom attached to a magnesium atom of the Grignard reagent is secondary carbon.

18. The process for producing tertiary phosphine as claimed in claim 2, wherein a carbon atom attached to a magnesium atom of the Grignard reagent is tertiary carbon.

19. The process for producing tertiary phosphine as claimed in claim 3, wherein a carbon atom attached to a magnesium atom of the Grignard reagent is tertiary carbon.

20. The process for producing tertiary phosphine as claimed in claim 3, wherein the copper compound is a copper halide or copper(II) acetylacetonate.

21. The process for producing tertiary phosphine as claimed in claim 3, wherein X of the dialkylphosphinous halide represented by the formula (1) is chlorine.

* * * * *